United States Patent [19]

Moss

[11] Patent Number: 4,816,254

[45] Date of Patent: Mar. 28, 1989

[54] OINTMENT FOR TREATING SKIN IRRITATIONS

[76] Inventor: Thomas D. Moss, Rte. 1, Box 498, Gilbertsville, Ky. 42044

[21] Appl. No.: 79,123

[22] Filed: Jul. 29, 1987

[51] Int. Cl.$^4$ .............................................. A61K 31/00
[52] U.S. Cl. ..................................... 424/145; 424/131; 424/148; 424/485; 514/494; 514/553; 514/782; 514/783; 514/865; 514/873; 514/886; 514/887; 514/969; 514/970
[58] Field of Search ............... 424/145, 131, 148, 485; 514/494, 553, 782, 783, 865, 873, 886, 887, 969, 970

[56] References Cited

U.S. PATENT DOCUMENTS

| | | | |
|---|---|---|---|
| 2,425,311 | 8/1947 | Fauley | 514/785 |
| 2,652,355 | 9/1953 | Ercoli et al. | 514/514 |
| 4,034,077 | 7/1977 | Hill et al. | 424/69 |
| 4,307,717 | 12/1981 | Hymes et al. | 424/485 |
| 4,507,321 | 3/1985 | Raisfeld | 514/673 |
| 4,556,560 | 12/1985 | Buckingham | 514/494 |

*Primary Examiner*—Maurice J. Welsh
*Assistant Examiner*—S. A. Acquah
*Attorney, Agent, or Firm*—King & Schickli

[57] ABSTRACT

The invention provides an ointment composition for treating skin irritations such as diaper rash and decubitus. The composition includes zinc oxide, boric acid, karaya gum, peruvian balsam, cod liver oil and an appropriate solvent and pharmaceutical carrier.

10 Claims, No Drawings

OINTMENT FOR TREATING SKIN IRRITATIONS

TECHNICAL FIELD

The present invention relates generally to an ointment for treating skin irritations and more particularly to an ointment specially adapted for treating diaper rash and decubitus.

BACKGROUND OF THE INVENTION

Diaper rash is a common ailment afflicting a majority of infants to varying degrees. When an infant wets, urine contacts the skin. Bacteria on the skin breaks down urea in this urine to form ammonia. This ammonia burns and irritates the infant's skin.

The ailment may be further compounded where the already irritated skin rubs against a diaper or other clothing. This chafing effect is particularly severe when the diaper in contact with the skin is wet.

Where the diaper rash is particularly severe, the infant may develop the added complications of decubitus wherein the skin breaks down. More specifically, the various layers of skin tissue die from the outside layer in. If not effectively treated, the condition can develop to the point of an open sore that is very susceptible to infection.

Numerous treatments have been developed for diaper rash. One such treatment is disclosed in U.S. Pat. No. 4,034,077 to Hill, et al. The Hill patent discloses ointments and powders includung sebacic acid as the active ingredient.

To the best of my knowledge, none of the currently available products for treating skin irritations such as diaper rash and decubitus are completely adequate. The inadequacies may be attributed to the fact that the treatments all seem to possess one or more of the following disadvantages. Many of the treatments fail to provide adequate skin protection. Thus, they fail to eliminate further skin irritation and facilitate the natural healing process. Others fail to resist removal when contacted by clothing and body fluids. Still others fail to provide acceptable results within a reasonable time period.

Just as importantly, presently available treatments are not adapted to successfully treat both diaper rash and decubitus simultaneously. Thus, infants suffering from both diaper rash and decubitus need treatment with multiple products. This drastically increases treatment costs, creates problems with compatibility of treatments and, thereby, complicates the treatment. A need is therefore identified for an improved composition for treating skin irritations of this type both more efficiently and effectively.

SUMMARY OF THE INVENTION

It is, accordingly, a primary object of the present invention to provide a composition for treating skin irritations overcoming the above-described limitations and disadvantages of the prior art.

Still another object of the present invention is to provide an ointment composition for treating skin irritations that is water repellent and adheres to the affected area despite contact with body fluids and/or clothing.

Yet another object of the present invention is to provide an ointment composition that does not permanently stain clothing with ordinary usage while providing a protective coating that enables the natural healing process to occur and prevents any additional skin irritation.

Another object of the present invention is to provide an ointment composition for more efficiently and effectively treating skin irritations such as diaper rash and decubitus.

Still another object of the present invention is to provide an ointment composition for effectively treating diaper rash and decubitus simultaneously.

Additional objects, advantages and other novel features of the invention will be set forth in part in the description that follows and in part will become apparent to those skilled in the art upon examination of the following or may be learned with the practice of the invention.

In satisfaction of the foregoing objects and advantages, there is provided by this invention an ointment composition for treating skin irritations. The ointment composition comprises by weight 1-20% zinc oxide, 0.5-10% boric acid, 5-15% karaya gum powder, 1-15% peruvian balsam, 1-15% cod liver oil, 1-15% solvent and 1-80% suitable pharmaceutical vehicle.

More preferably, the composition comprises 5-10% zinc oxide, 1-3% boric acid, 8-12% karaya gum powder, 5-10% peruvian balsam, 5-10% cod liver oil, 10-20% solvent and 40-60% pharmaceutical vehicle.

Preferably, the solvent is an alcohol that is utilized to make a suspension with the karaya gum powder during ointment composition processing. Propylene glycol is particularly adapted for this purpose.

The pharmaceutical vehicle may be any appropriate carrier or emollient known in the art. White ointment is an example of one such vehicle that may be utilized in the ointment composition of the present invention. The white ointment may also be mixed with mineral oil to provide the ointment composition of the present invention with the proper consistency for spreading and the desired emollient properties.

The shelf life of the present ointment may also be extended by including a pharmaceutical preserving agent in the composition. Examples of such agents include methyl paraben and benzyl alcohol.

Advantageously, the ointment composition of the present invention is water repellent and readily adheres to the affected area being treated despite repeated contact with body fluids and/or clothing. Further, the ointment does not permanently stain clothing with ordinary usge. The zinc oxide provides antiseptic activity and the boric acid provides antibacterial activity. The peruvian balsam advantageously promotes growth of the epithelial cells and the cod liver oil provides the skin with vitamins A and D while also stabilizing the balsam.

When mixed together, the components of the ointment composition provide a protective coating that enables the natural healing process to occur and prevents any additional irritation to the inflamed skin. Advantageously, the ointment also efficiently and effectively treats both diaper rash and decubitus simultaneously. Thus, where these conditions coexist, the ointment of the present invention eliminates the need for treatment with multiple products. This advantageously reduces treatment costs and eliminates the problems of finding compatible treatments for these two afflictions.

DETAILED DESCRIPTION OF THE INVENTION

To achieve the foregoing and other objects and in accordance with the purposes of the present invention as described herein, an improved ointment composition is provided. The composition comprises in weight percentages 1-20% zinc oxide, 0.5-10% boric acid, 5-15% karaya gum powder, 1-15% peruvian balsam, 1-15% cod liver oil, 1-25% solvent and 1-80% pharmaceutical vehicle.

Suitable solvents include certain alcohols, such as propylene glycol that may be used as a suspending agent to make a suspension with the karaya gum powder.

A suitable pharmaceutical vehicle includes those known carriers and/or emollients that do not react with the other components of the ointment composition. A specific example of such a vehicle includes white ointment. The white ointment may be further mixed with mineral oil to provide the proper consistency for spreading the ointment of the present invention over the skin. The mineral oil, of course, also acts as an emollient to further sooth the irritated skin.

Certain ointment compositions within the range and scope of the present invention may require the addition of pharmaceutical preserving agents to improve and prolong shelf life. Examples of agents that may be utilized for this purpose include methyl paraben and benzyl alcohol.

In the most preferred embodiment, the ointment composition for treating skin irritations such as diaper rash and decubitus includes 5-10% zinc oxide, 1-3% boric acid, 8-12% karaya gum powder, 5-10% peruvian balsam, 5-10% cod liver oil, 10-20% solvent such as propylene glycol and 40-60% pharmaceutical vehicle such as white ointment and/or white ointment and mineral oil. Again, these percentages are expressed as weight percents of the final composition.

While appropriate for treating a number of skin irritations, the ointment composition of the present invention is particularly adapted to treating diaper rash and decubitus either singularly or simultaneously. As should be appreciated, the ointment composition provides both antiseptic and antibacterial activity by means of the zinc oxide and boric acid components. These work quickly to relieve and eliminate the stinging pain of diaper rash and promote rapid healing of both diaper rash and decubitus. Advantageously, the peruvian balsam promotes the growth of epithelial cells. The cod liver oil stabilizes the peruvian balsam and provides vitamins A and D to the skin to further support rapid, scar-free healing.

The ointment is specifically adapted for application directly to the area of the skin requiring treatment. More specifically, the treatment area is first gently cleaned by, for example, carefully dabbing with a damp cloth. This cleaning would include the removing of any previously applied ointment. The treatment area is then dried and fresh ointment applied sparingly. Application may be performed by hand but preferably with a suitable medical applicator or swab. Application of the ointment is repeated three or four times a day until the diaper rash or decubitus has healed.

The following examples are presented to further illustrate the invention, but it should be recognized that the invention is not to be considered as limited thereto.

EXAMPLE 1

60 grams of zinc oxide ointment, 20% USP are mixed together with 30 grams of boric acid ointment, 10% in a first container. In a second container, 25 cc's or approximately 25.9 grams of propylene glycol are added to 15 grams of karaya gum powder, NF. The propylene glycol and karaya gum powder are thoroughly mixed so as to form a suspension smooth and free of granules. The mixtures in the first two containers are then thoroughly mixed together so as to again be smooth and free of granules. Next, 10 cc's or approximately 11.6 grams of peruvian balsam, NF is added to the mixture. 10 l cc's or approximately 9.23 grams of cod liver oil, NF is also added to the mixture. The mixture is then thoroughly mixed to produce an ointment composition for treating skin irritations.

EXAMPLE 2

60 grams of zinc oxide ointment, 20% USP is mixed together with 30 grams of boric acid ointment, 10% in a first container just as described above in Example 1. 15 cc's or approximately 15.54 grams of propylene glycol are then added to and mixed with 15 grams of karaya gum powder in a second container so as to form a suspension. The suspension is thoroughly mixed until it is smooth and free of granules. The mixtures in the two containers are then added together and thoroughly mixed as described above in Example 1. 10 cc's of peruvian balsam NF and 10 cc's of cod liver oil NF are then added to and mixed into the ointment composition. In order to further improve and prolong shelf life, 300 milligrams of methyl paraben are then added and mixed into the ointment composition. The composition may then be stored in a jar or tube for an extended period of time and utilized to treat skin irritations such as diaper rash and decubitus as necessary.

In summary, numerous benefits have been described which result from employing the concepts of the present invention. A novel ointment composition including effective amounts of an antiseptic agent, zinc oxide, and an antibacterial agent, boric acid, is disclosed. The ointment composition is particularly useful in treating skin irritations such as diaper rash and decubitus, both singularly and simultaneously. Advantageously, the ointment composition promotes rapid healing by coating the afflicted area and resisting removal despite contact with body fluids and clothing. In addition, the ointment does not permanently stain clothing with ordinary use. Thus, the ointment may be utilized with cloth as well as disposable diapers.

The invention has been described herein with reference to a preferred ointment composition. However, as obvious variations thereon will become apparent to those skilled in the art, the invention is not to be considered as limited thereto.

I claim:

1. An ointment composition for treating skin irritations comprising: 1 to 20% zinc oxide, 0.5 to 10% boric acid, 5 to 15% karaya gum powder, 1 to 15% peruvian balsam, 1 to 15% cod liver oil, 1 to 25% solvent and 1 to 80% pharmaceutical vehicle; all percentages expressed by weight of the final composition; said composition providing both antiseptic and antibacterial activity while promoting growth of epithelial cells and rapid scar-free healing so as to allow quick and effective treatment of both diaper rash and decubitus.

2. The composition set forth in claim 1, wherein said solvent is an alcohol.

3. The composition set forth in claim 1, wherein said solvent is propylene glycol.

4. The composition set forth in claim 1, wherein said pharmaceutical vehicle is white ointment.

5. The composition set forth in claim 1, wherein said ointment also includes a pharmaceutical preserving agent.

6. An ointment composition for treating skin irritations, comprising: 5-10% zinc oxide, 1-3% boric acid, 8-12% karaya gum powder, 5-10% peruvian balsam, 5-10% cod liver oil, 10-20% solvent and 40-60% pharmaceutical vehicle; all percentages expressed by weight of the final composition; said composition providing both antiseptic and antibacterial activity while promoting growth of epithelial cells and rapid scar-free healing so as to allow quick and effective treatment of both diaper rash and decubitus.

7. The composition set forth in claim 6, wherein said solvent is an alcohol.

8. The composition set forth in claim 6, wherein said solvent is propylene glycol.

9. The composition set forth in claim 6, wherein said pharmaceutical vehicle is white ointment.

10. The composition set forth in claim 6, wherein said ointment also includes a pharmaceutical preserving agent.

* * * * *